US009509890B2

(12) United States Patent
Nakayama

(10) Patent No.: US 9,509,890 B2
(45) Date of Patent: Nov. 29, 2016

(54) SOLID IMAGE PICKUP APPARATUS

(75) Inventor: Takashi Nakayama, Ina (JP)

(73) Assignee: OLYMPUS CORPORATION, Tokyo (JP)

(*) Notice: Subject to any disclaimer, the term of this patent is extended or adjusted under 35 U.S.C. 154(b) by 1180 days.

(21) Appl. No.: 13/032,839

(22) Filed: Feb. 23, 2011

(65) Prior Publication Data
US 2011/0211053 A1 Sep. 1, 2011

(30) Foreign Application Priority Data

Feb. 26, 2010 (JP) ................. 2010-042900

(51) Int. Cl.
H04N 5/335 (2011.01)
H04N 5/225 (2006.01)
A61B 1/05 (2006.01)

(52) U.S. Cl.
CPC ............ H04N 5/2254 (2013.01); A61B 1/051 (2013.01)

(58) Field of Classification Search
CPC ............................ H04N 5/2254; A61B 1/051
USPC ............................. 348/65, 76; 600/130, 176
IPC ....................................................... H04N 7/18
See application file for complete search history.

(56) References Cited

U.S. PATENT DOCUMENTS

| 5,381,176 A * | 1/1995 | Tanabe ................. G11B 31/006 348/273 |
| 2007/0055104 A1* | 3/2007 | Kumei et al. ................. 600/176 |
| 2009/0043166 A1* | 2/2009 | Ishii ............................... 600/130 |
| 2009/0051763 A1* | 2/2009 | Adler et al. .................... 348/65 |

FOREIGN PATENT DOCUMENTS

JP 2009-176815 8/2009

* cited by examiner

Primary Examiner — Neil Mikeska
(74) Attorney, Agent, or Firm — Scully, Scott, Murphy & Presser, P.C.

(57) ABSTRACT

A solid image pickup apparatus according to an embodiment includes: a device chip including a first principal surface and a second principal surface, a CMOS device and an electrode portion being formed on the first principal surface; a holding block including a joining surface joined to the second principal surface and an inclined surface inclined inward at a predetermined angle relative to the joining surface; a wiring board including a distal end portion including a connection portion connected to the electrode portion on the first principal surface, an extending portion that is in contact with the inclined surface, the extending portion being joined to the inclined surface via a bonding layer; and a flexure portion flexed at the predetermined angle between the distal end portion and the extending portion.

17 Claims, 4 Drawing Sheets

SOLID IMAGE PICKUP APPARATUS

CROSS REFERENCE TO RELATED APPLICATION

This application claims the benefit of Japanese Application No. 2010-042900 filed in Japan on Feb. 26, 2010, the contents of which are incorporated herein by this reference.

BACKGROUND OF THE INVENTION

1. Field of the Invention

Embodiments of the present invention relate to a solid image pickup apparatus including an image pickup device substrate with a solid image pickup device formed thereon, and a wiring board including a joining portion joined to the image pickup device substrate, a flexure portion flexed at a predetermined angle and an extending portion, and specifically relates to a solid image pickup apparatus including a holding portion that holds the flexure portion at the predetermined angle.

2. Description of the Related Art

Electronic endoscopes with a solid image pickup apparatus (hereinafter also referred to as "image pickup apparatus") included in a distal end portion of an insertion portion thereof have been used. However, for provision of an insertion portion with a small diameter, there is only a limited space for the distal end portion of the insertion portion including the image pickup apparatus therein. Therefore, connection between the image pickup device substrate with an image pickup device formed thereon and a wiring board for transmitting, e.g., image signals from the image pickup device and arrangement of the wiring board are important.

The present applicants have disclosed a structure including a flexure portion fowled therein, the flexure portion being flexed at a predetermined angle by bringing electronic components mounted on a wiring substrate into contact with each other, in Japanese Patent Application Laid-Open Publication No. 2009-176815.

SUMMARY OF THE INVENTION

A solid image pickup apparatus according to an aspect of the present invention includes: an image pickup device substrate including a first principal surface and a second principal surface, a solid image pickup device being formed on the first principal surface; a holding portion including a joining surface joined to the second principal surface of the image pickup device substrate, and an inclined surface inclined inward at a predetermined angle relative to the joining surface; and a wiring board including a distal end portion joined to the image pickup device substrate, an extending portion jointed to the inclined surface via a bonding layer, and a flexure portion flexed at the predetermined angle between the distal end portion and the extending portion.

An endoscope apparatus according to another aspect of the present invention includes: an image pickup device substrate disposed in a distal end portion of an insertion portion thereof, the image pickup device substrate including a first principal surface and a second principal surface, a solid image pickup device being formed on the first principal surface; a holding portion including a joining surface joined to the second principal surface of the image pickup device substrate, and an inclined surface inclined inward at a predetermined angle relative to the joining surface; and a wiring board including a distal end portion joined to the image pickup device substrate, an extending portion jointed to the inclined surface via a bonding layer, and a flexure portion flexed at the predetermined angle between the distal end portion and the extending portion.

DETAILED DESCRIPTION OF THE PREFERRED EMBODIMENTS

<First Embodiment>

Figure 1:
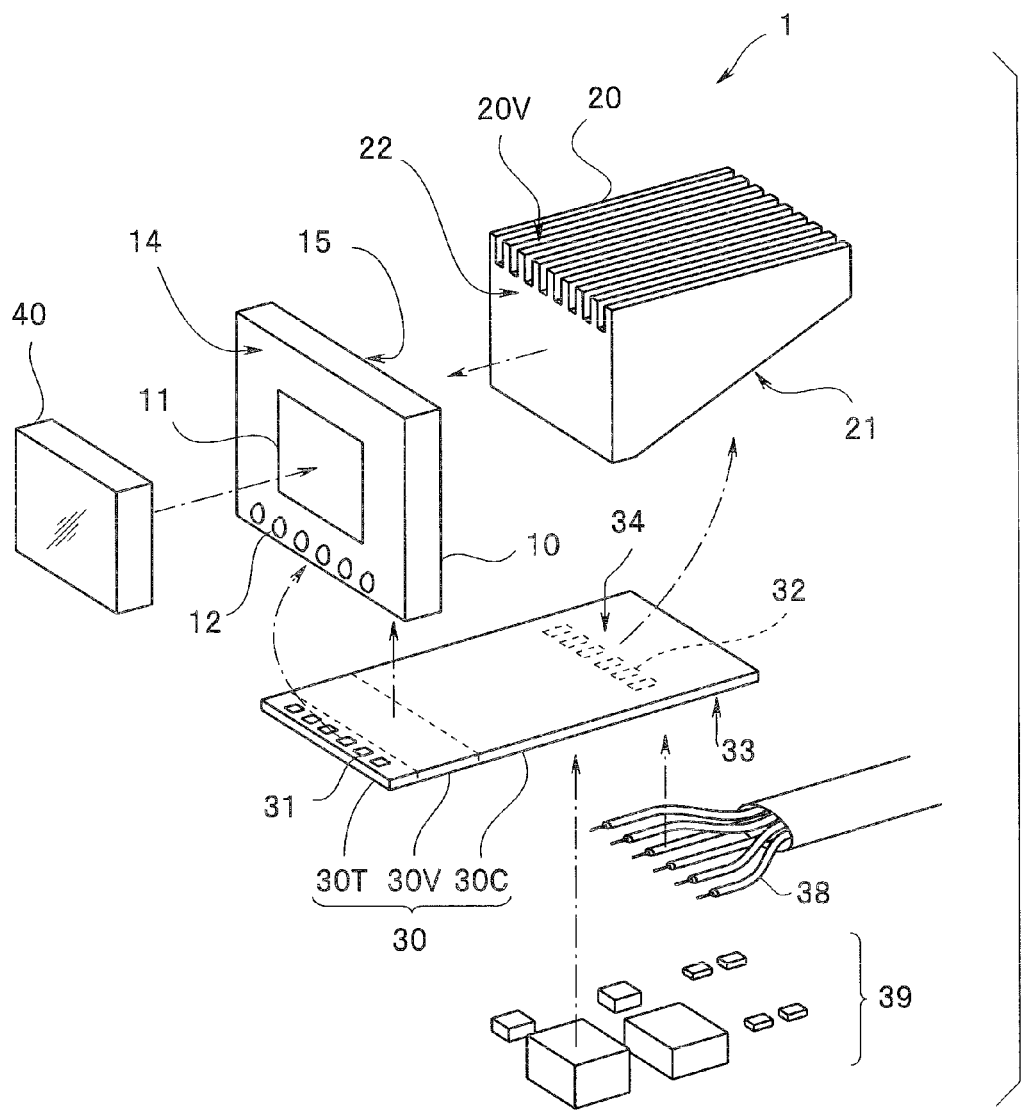
FIG. 1 is an exploded diagram illustrating a structure of an image pickup apparatus according to a first embodiment.
Figure 2:
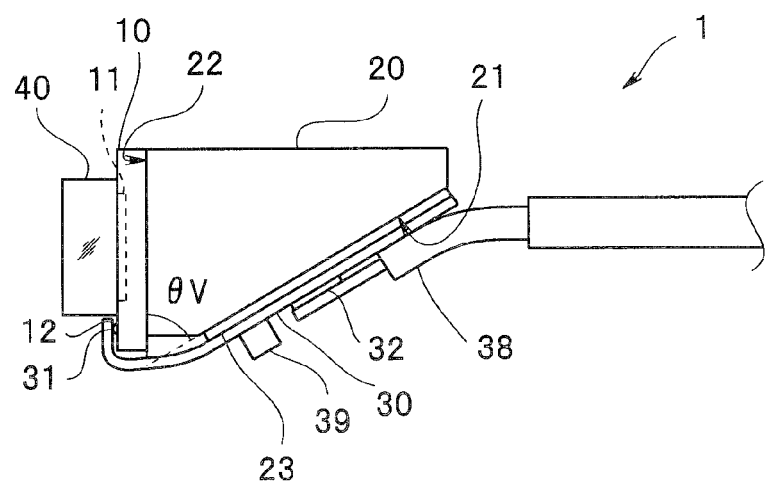
FIG. 2 is a diagram illustrating a side view of a structure of the image pickup apparatus according to the first embodiment.

As illustrated in FIGS. 1 and 2, a solid image pickup apparatus 1 according to the present embodiment includes a device chip 10, which is an image pickup device substrate, a holding block 20, which is a holding portion, a wiring board 30, a protective glass 40, and a cable 38.

The device chip 10, which is an imager, includes a first principal surface 14 and a second principal surface 15 and a CMOS device 11, which is a solid image pickup device, and an electrode portion 12 are formed on the first principal surface 14. On the electrode portion 12, which includes external input/output terminals for the CMOS device 11, for example, protruding bumps are formed. The protective glass 40 is a transparent substrate that protects the CMOS device 11. The solid image pickup device may be, e.g., a CCD.

The wiring board 30, which includes a flexible resin of, e.g., polyimide as a base material, includes a front surface 33 and a back surface 34. The wiring board 30 also includes a wiring layer (not illustrated) including, e.g., copper, a connection portion 31 exposed at the back surface 34, and a connection portion 32 exposed at the front surface 33, and a connection portion (not illustrated) exposed at the front surface 33, the connection portion being provided for mounting electronic components 39. The wiring board 30 connects the device chip 10 and a cable 38 including conductor wires. The wiring board 30, which is a multilayer wiring board including at least wiring layers on two surfaces thereof, includes a through wire (not illustrated) extending through an inner part of the wiring board 30. The electronic components 39 such as a chip capacitor are mounted on the front surface 33, forming an electronic circuit. Although for ease of description, the wiring board 30 is expressed by dividing the wiring board 30 into a distal end portion 30T, a flexure portion 30V and an extending portion 30C, as illustrated in FIG. 1, the wiring board 30 according to the present embodiment is a single wiring board, and thus, the boundaries between the divisions are not clearly defined. In the wiring board, it is only necessary that at least the flexure portion 30V have flexibility, and thus, the distal end portion 30T and the extending portion 30C may be formed by a rigid substrate. In the case of a wiring board including a flexible substrate and rigid substrates, the boundaries between the divisions are clear. The cable 38, which includes a plurality of conductor wires, transmits signals between the device chip 10 and, e.g., a control unit and a signal processing unit (not illustrated).

The image pickup apparatus 1 includes the holding block 20, which is a holding portion for stably holding the wiring board 30 at a predetermined angle relative to the device chip 10. The holding block 20 includes a joining surface 22 joined to the second principal surface 15 of the device chip 10, and an inclined surface 21 inclined inward at a predetermined angle θV relative to the joining surface 22. As illustrated in FIG. 2, the angle θV of the inclined surface 21 determines a flexion angle of the wiring board 30, and where the angle θV is less than 90 degrees, the inclined surface 21 is inclined inward. The angle θV is preferably 20 to 45 degrees, and more preferably 25 to 35 degrees, for example, 30 degrees. The angle θV within the aforementioned range enables downsizing of the image pickup apparatus 1 as described later.

The holding block 20 functions as a fixing member that fixes the wiring board 30, which has flexibility, in a predetermined space, that is, in a projection space for the device chip 10. Furthermore, the holding block 20 stably holds the wiring board 30, facilitating the work for joining the cable 38 to the wiring board 30. The holding block 20 also serves as a heatsink having a heat dissipation function that dissipates heat generated by, e.g., the device chip 10. As illustrated in FIG. 1, the surface area of the holding block 20 is increased by forming grooves 20V on a surface of the holding block 20, enabling enhancement of the heat dissipation function. If a focus is placed on the heat dissipation function, the holding block 20 preferably includes a material having high thermal conductivity, such as aluminum. In the image pickup apparatus 1, since the holding block 20 has a heat dissipation function, the device chip 10 operates stably.

Furthermore, the holding block 20 functions as a reinforcing member that holds the device chip 10 and the wiring board 30 in an integrated manner for mechanical strength enhancement. In other words, since the device chip 10 includes, for example, a silicon substrate, the device chip 10 may be deformed or broken by an external force. However, the device chip 10 is strengthened as a result of the holding block 20 being joined to the device chip 10. The wiring board 30 is also strengthened as a result of the wiring board 30 being joined to the holding block 20, although the wiring board 30 substantially loses its flexibility.

As described above, in the image pickup apparatus 1 according to the present embodiment, the wiring board 30 is fixed in contact with the holding block 20, and thus, consistently flexed at the predetermined angle. In other words, the image pickup apparatus 1 enables arrangement of the wiring board 30 in a predetermined small space, and thus, enables easy reduction in outer size. Accordingly, the image pickup apparatus 1 can stably be disposed in a predetermined small space.

Next, a method for manufacturing the image pickup apparatus 1 will be described. The device chip 10, the holding block 20, the wiring board 30, the protective glass 40 and the cable 38 are individually prepared and then integrated in an assembly process.

The device chip 10 is prepared by cutting a silicon substrate into pieces after forming multiple CMOS devices 11 and electrode portions 12 on the silicon substrate by means of a known semiconductor process. The holding block 20 is prepared by a machining process where the holding block 20 includes a metal such as aluminum, or is prepared by molding where the holding block 20 includes, e.g., a heat resistant resin. The wiring board 30 is prepared by sticking a copper foil and polyimide, which is a base material, together and then performing etching, or using, e.g., a plating method.

In the assembly process, for example, first, the protective glass 40 is joined to the first principal surface 14 of the device chip 10, and the joining surface 22 of the holding block 20 is joined to the second principal surface 15 of the device chip 10. For the joining, a bonding agent (not illustrated) is used. It is unnecessary that the joining surface 22 of the holding block 20 should have a size that is the same as that of the second principal surface 15 of the device chip 10.

Next, e.g., a nonconductive paste NCP is applied to at least one of an area around the electrode portion 12 on the first principal surface 14 of the device chip 10 and a back surface of the distal end portion 30T of the wiring board 30. Then, the distal end portion 30T of the wiring board 30 is joined to the device chip 10 by means of alignment/pressure bonding/cure treatment of the electrode portion 12 and the connection portion 31, thereby the electrode portion 12 and the connection portion 31 being electrically connected. At this stage, the flexure portion 30V and the extending portion 30C of the wiring board 30 lie on a plane that is the same as the first principal surface 14 of the device chip 10 as with distal end portion 30T. In other words, the flexion angle of the flexure portion 30V is 0 degrees.

Next, a bonding agent, which becomes a bonding layer 23, is applied to at least one of the back surface 34 side of the extending portion 30C of the wiring board 30 and the inclined surface 21 of the holding block 20, and then the flexure portion 30V of the wiring board 30 is flexed so that the extending portion 30C is brought into contact with the inclined surface 21 of the holding block 20. The bond agent is cured in a state in which the extending portion 30C is in contact with the inclined surface 21 of the holding block 20, thereby the extending portion 30C being joined to the inclined surface 21 via the bonding layer 23. The space between the flexure portion 30V and the device chip 10 may be an empty space or may be charged with, e.g., a bond agent, which is the same as one used for the bonding layer 23.

In the image pickup apparatus 1, the flexion angle of the wiring board 30 is determined by the angle of the inclined surface 21 of the holding block 20, and thus, the wiring board 30 can easily and accurately be flexed at the predetermined angle. Furthermore, since the wiring board 30 is in contact with the holding block 20 by means of surface contact over a wide contact area, the wiring board 30 can easily be flexed and is not subjected to undue stress, and thus unlikely to be broken.

Lastly, the conductor wires in the cable 38 are electrically connected to the connection portion 32 of the wiring board 30 by means of, for example, solder bonding. In the image pickup apparatus 1 the wiring board 30 is stably held by the holding block 20, and thus, the cable 38 can easily be soldered to the connection portion 32. In addition, there is no need to use a particular fixture for temporarily fixing the wiring board 30 when the soldering is performed. In the image pickup apparatus 1, the cable 38 including the conductor wires is connected to the front surface 33 of the extending portion 30C of the wiring board 30, which is a surface opposite a joining surface (back surface 34) joined to the bonding layer 23, which provides good workability and thus, work mistakes are less likely to occur, resulting in provision of a high manufacture yield.

As described above, the wiring board 30 includes the distal end portion 30T joined to the first principal surface 14 of the device chip 10, the extending portion 30C joined to the inclined surface 21 of the holding block 20 via the bonding layer 23, and the flexure portion 30V flexed at the predetermined angle between the distal end portion 30T and the extending portion 30C. The device chip 10 includes the electrode portion 12 for the CMOS device 11 on the first principal surface 14, and the connection portion 31 of the wiring board 30 is connected to the electrode portion 12.

<Variation of First Embodiment>

Next, an image pickup apparatus 1A according to a variation of the first embodiment will be described. Since the image pickup apparatus 1A according to the present variation is similar to the image pickup apparatus 1 according to the first embodiment, components that are the same as those of the image pickup apparatus 1 are provided with the same reference numerals as those of the image pickup apparatus 1, and a description thereof will be omitted.

Figure 3:
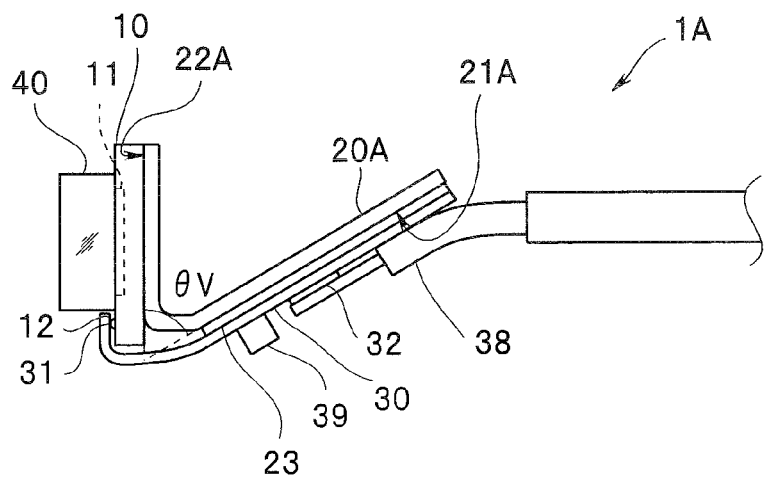
FIG. 3 is a diagram illustrating a side view of a structure of an image pickup apparatus according to a variation of the first embodiment.

As illustrated in FIG. 3, a holding portion of the image pickup apparatus 1A is an L-shaped plate material 20A. The L-shaped plate material 20A, which is a plate material flexed at a predetermined angle, includes a joining surface 22A joined to a second principal surface 15 of a device chip 10, and an inclined surface 21A inclined inward at a predetermined angle θV relative to the joining surface 22A as with the holding block 20.

Instead of the L-shaped plate material 20A, e.g., a U-shaped plate material including a surface parallel to the joining surface 22, or a hollow holding block may be employed for the holding portion.

The image pickup apparatus 1A according to the present variation provides advantages that are similar to those of the image pickup apparatus 1 according to the first embodiment. The image pickup apparatus 1A is somewhat inferior to the image pickup apparatus 1 in terms of its function that dissipates heat from the joining surface 22A, but is lighter than the image pickup apparatus 1.

<Second Embodiment>

Next, the image pickup apparatus 1B according to the second embodiment will be described. Since the image pickup apparatus 1B according to the present embodiment is similar to the image pickup apparatus 1 according to the first embodiment, components that are the same as those of the image pickup apparatus 1 are provided with the same reference numerals as those of the image pickup apparatus 1, and a description thereof will be omitted.

Figure 4:
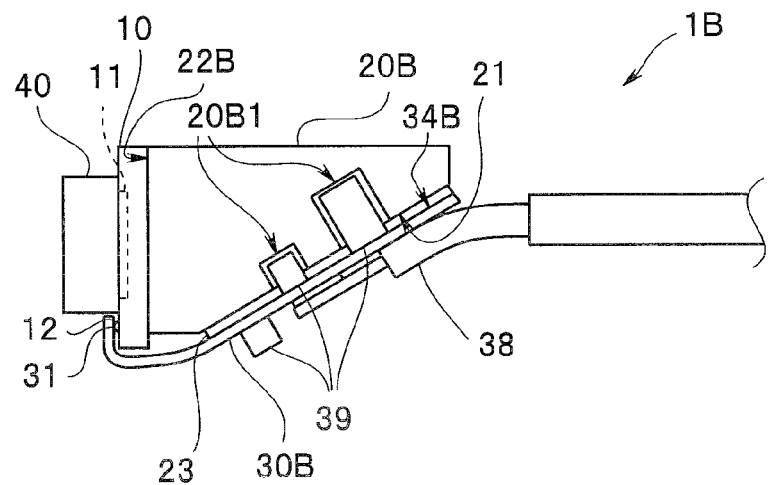
FIG. 4 is a diagram illustrating a side view of a structure of an image pickup apparatus according to a second embodiment.

As illustrated in FIG. 4, a wiring board 30B of the image pickup apparatus 1B according to the present embodiment includes electronic components 39 mounted not only on a front surface 33 but also on a back surface 34. Meanwhile, the holding block 20B, which is a holding portion, includes recess portions 20B1 at an inclined surface 21B. The electronic components 39 mounted on the back surface 34B of the wiring board 30B are accommodated in the recess portions 20B1 of the inclined surface 21B. In other words, the recess portions 20B1 are spaces for holding the electronic components 39. Accordingly, the wiring board 30B has a high degree of freedom in arrangement of the electronic components 39 and can easily be designed. Furthermore, heat generated by the electronic components 39 is dissipated via a joining surface 22B of the holding block 20B. In addition, large electronic components can be mounted on the wiring board 30B. The gaps between the recess portions 20B1 and the electronic components 39 may be empty spaces (air), or may be charged with, e.g., a bonding agent that is the same as one used for the bonding layer 23.

As described above, the image pickup apparatus 1B according to the present embodiment provides mounting of the electronic components 39 with a higher density in addition to the advantages provided by the image pickup apparatus 1. Furthermore, the image pickup apparatus 1B enables provision of the holding block 20B of a size smaller than the holding block 20, and thus, can be arranged in a space smaller than the space required for the image pickup apparatus 1.

<Variation of the Second Embodiment>

Next, an image pickup apparatus 1C according to a variation of the second embodiment will be described. Since the image pickup apparatus 1C according to the present variation is similar to the image pickup apparatus 1B according to the second embodiment, components that are the same as those of the image pickup apparatus 1B are provided with the same reference numerals as those of the image pickup apparatus 1B, and a description thereof will be omitted.

Figure 5:
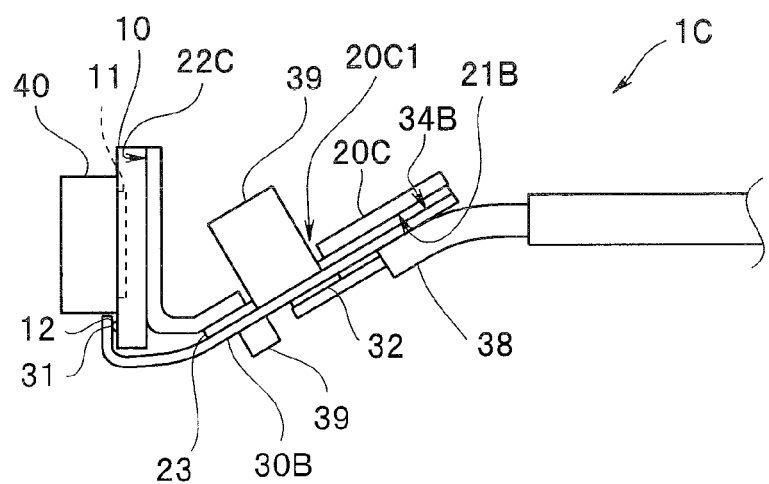
FIG. 5 is a diagram illustrating a side view of a structure of an image pickup apparatus according to a variation of the second embodiment.

As illustrated in FIG. 5, a holding portion of the image pickup apparatus 1C according to the present variation is an L-shaped plate material 20C including a hole 20C1 at an inclined surface 21C. The hole 20C1 has a size larger than the size of an electronic component 39 mounted on a back surface 34B of a wiring board 30B. Accordingly, the electronic component 39 mounted on the back surface 34B of the wiring board 30B is accommodated via the hole 20C1.

As described above, the image pickup apparatus 1C according to the present variation provides advantages provided by the image pickup apparatus 1B according to the second embodiment. The image pickup apparatus 1C is somewhat inferior to the image pickup apparatus 1B in terms of its function that dissipates heat from a joining surface 22C, but is lighter than the image pickup apparatus 1B.

<Third Embodiment>

Figure 6:
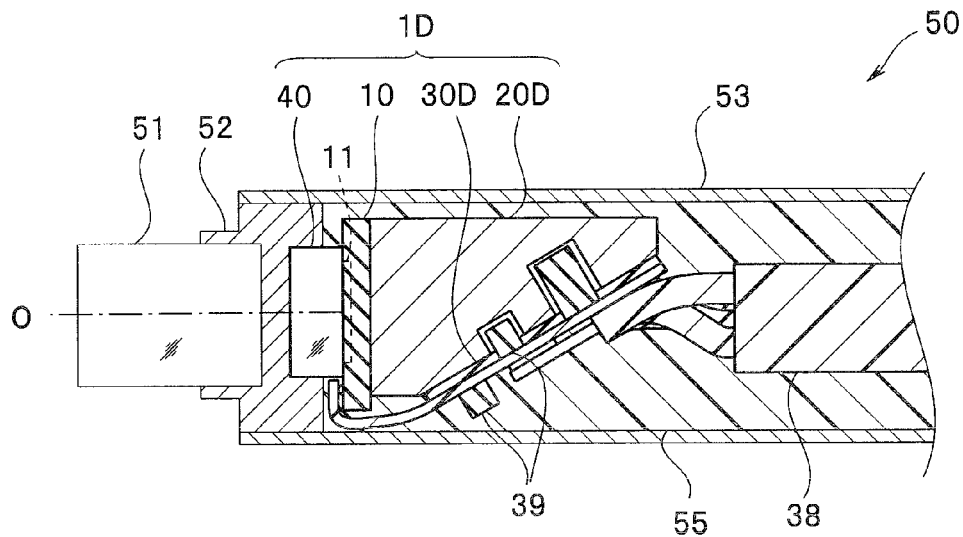
FIG. 6 is a diagram illustrating a cross-sectional structure of an endoscope including an image pickup apparatus according to a third embodiment.

Next, an endoscope apparatus 50 with an image pickup apparatus 1D incorporated in a distal end portion of an insertion portion thereof will be described as a third embodiment. An optical system 51 and the image pickup apparatus 1D, which are schematically illustrated in FIG. 6, are fixed by a frame portion 52 with an optical axis O as a center. The back side of the image pickup apparatus 1D is covered by a shield frame 53, and an inner portion of the shield frame 53 is charged with a filler 55 including a nonconductive resin with high thermal conductivity. A chip component 56 is mounted on an extending portion 30C of the wiring board 30D, and a cable 38 is connected to a connection portion 32.

The image pickup apparatus 1D has a structure similar to that of the image pickup apparatus 1B, which has already been described.

The endoscope apparatus 50 having the above structure, that is, having, e.g., the image pickup apparatus 1D in the distal end portion of the insertion portion thereof enables provision of a reduced diameter.

<Fourth Embodiment>

Finally, an image pickup apparatus 1E according to the fourth embodiment will be described. Since the image pickup apparatus 1E according to the present embodiment is similar to the image pickup apparatus 1 according to the first embodiment, components that are the same as those of the image pickup apparatus 1 are provided with the same reference numerals as those of the image pickup apparatus 1, and a description thereof will be omitted.

Figure 7:
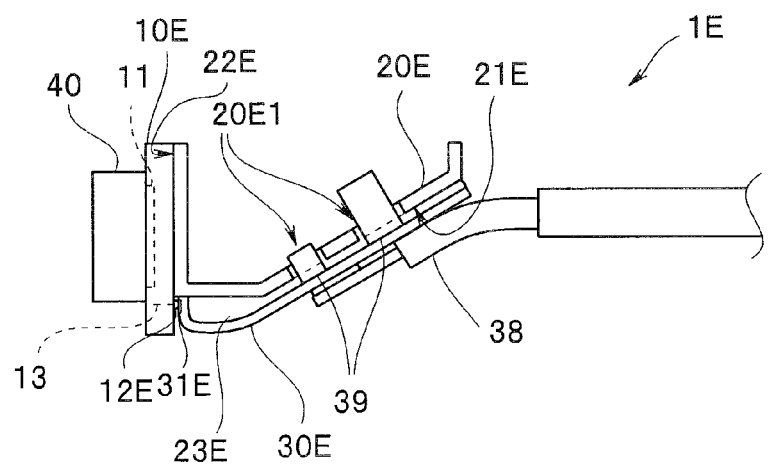
FIG. 7 is a diagram illustrating a side view of a structure of an image pickup apparatus according to a fourth embodiment.

As illustrated in FIG. 7, a device chip 10E in the image pickup apparatus 1E according to the present embodiment is a chip used for what is called chip size package, which includes a through wire 13, and an electrode portion 12E on a second principal surface 15. A connection portion 31E is formed on a front surface 33 of a wiring board 30E. A joining surface 22E of a U-shaped plate material 20E, which is a holding portion, is joined to a device chip 10E, and an inclined surface 21E of the U-shaped plate material 20E is joined to the wiring board 30E. The U-shaped plate material 20E includes holes 20E1 for disposing electronic components 39 at the inclined surface 21E. As illustrated in FIG. 7, a flexure portion may be fixed to the device chip 10E via a bonding layer 23E.

The wiring board 30E includes a distal end portion joined to the device chip 10E, an extending portion joined to the inclined surface 21E via the bonding layer 23E, and the flexure portion flexed at a predetermined angle between the distal end portion and the extending portion. The device chip 10E includes the electrode portion 12E for a CMOS device 11 on the second principal surface 15, and the connection portion 31E of the wiring board 30E is connected to the electrode portion 12E.

The image pickup apparatus 1E according to the present embodiment provides advantages that are the same as those of, e.g., the image pickup apparatus 1C according to the variation of the second embodiment, and further enables provision of a reduced diameter.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. A solid image pickup apparatus comprising:
    an image pickup device substrate including a first principal surface and a second principal surface, a solid image pickup device being formed on the first principal surface;
    a holding portion including a joining surface directly joined to the second principal surface of the image pickup device substrate, and an inclined surface inclined inward at a predetermined angle relative to the joining surface; and
    a wiring board including a distal end portion, an extending portion and a flexible portion disposed between the distal end portion and extending portion, the distal end portion being joined to the image pickup device substrate, the extending portion being jointed to the inclined surface of the holding portion via a bonding layer, and the flexure portion being flexed at the predetermined angle to permit the extending portion to be jointed to the inclined surface.

2. The solid image pickup apparatus according to claim 1, wherein the holding portion includes a block having a heat dissipation function.

3. The solid image pickup apparatus according to claim 2, wherein the holding portion includes a recess portion or a through hole at the inclined surface;
    wherein the wiring board is a multilayer wiring board including at least a wiring layer on each of two surfaces thereof, an electronic component being mounted on each of the two surfaces; and
    wherein the electronic component mounted on the surface on the bonding layer side is disposed in the recess portion or via the through hole.

4. The solid image pickup apparatus according to claim 1, wherein the holding portion is an L-shaped plate material.

5. The solid image pickup apparatus according to claim 4, wherein the holding portion includes a recess portion or a through hole at the inclined surface;
    wherein the wiring board is a multilayer wiring board including at least a wiring layer on each of two surfaces thereof, an electronic component being mounted on each of the two surfaces; and
    wherein the electronic component mounted on the surface on the bonding layer side is disposed in the recess portion or via the through hole.

6. The solid image pickup apparatus according to claim 1, wherein an electrode portion for the solid image pickup device is formed on the first principal surface of the image pickup device substrate; and
    wherein a connection portion of the wiring board is connected to the electrode portion on the image pickup device substrate.

7. The solid image pickup apparatus according to claim 1, wherein the image pickup device substrate includes a through wire and an electrode portion for the solid image pickup device is formed on the second principal surface of the image pickup device substrate; and
    wherein a connection portion of the wiring board is connected to the electrode portion on the image pickup device substrate.

8. The solid image pickup apparatus according to claim 1, wherein a conductor wire is connected to a surface of the extending portion opposite a joining surface of the extending portion joined to the bonding layer.

9. An endoscope apparatus comprising:
    an image pickup device substrate disposed in a distal end portion of an insertion portion thereof, the image pickup device substrate including a first principal surface and a second principal surface, a solid image pickup device being formed on the first principal surface;
    a holding portion including a joining surface directly joined to the second principal surface of the image pickup device substrate, and an inclined surface inclined inward at a predetermined angle relative to the joining surface; and
    a wiring board including a distal end portion, an extending portion and a flexible portion disposed between the distal end portion and extending portion, the distal end portion being joined to the image pickup device substrate, the extending portion being jointed to the inclined surface of the holding portion via a bonding layer, and the flexure portion being flexed at the predetermined angle to permit the extending portion to be jointed to the inclined surface.

10. The endoscope apparatus according to claim 9, wherein the holding portion includes a block having a heat dissipation function.

11. The endoscope apparatus according to claim 10, wherein the holding portion includes a recess portion or a through hole at the inclined surface;
    wherein the wiring board is a multilayer wiring board including at least a wiring layer on each of two surfaces thereof, an electronic component being mounted on each of the two surfaces; and wherein the electronic component mounted on the surface on the bonding layer side is disposed in the recess portion or via the through hole.

12. The endoscope apparatus according to claim 10, wherein the holding portion is an L-shaped plate material.

13. The endoscope apparatus according to claim 12,
wherein the holding portion includes a recess portion or a through hole at the inclined surface;
wherein the wiring board is a multilayer wiring board including at least a wiring layer on each of two surfaces thereof, an electronic component being mounted on each of the two surfaces; and
wherein the electronic component mounted on the surface on the bonding layer side is disposed in the recess portion or via the through hole.

14. The endoscope apparatus according to claim 9,
wherein an electrode portion for the solid image pickup device is formed on the first principal surface of the image pickup device substrate; and
wherein a connection portion of the wiring board is connected to the electrode portion on the image pickup device substrate.

15. The endoscope apparatus according to claim 9,
wherein the image pickup device substrate includes a through wire and an electrode portion for the solid image pickup device is formed on the second principal surface of the image pickup device substrate; and
wherein a connection portion of the wiring board is connected to the electrode portion on the image pickup device substrate.

16. The endoscope apparatus according to claim 9,
wherein a conductor wire is connected to a surface of the extending portion opposite a joining surface of the extending portion joined to the bonding layer.

17. A solid image pickup apparatus comprising:
an image pickup device substrate including a first principal surface and a second principal surface, a solid image pickup device being formed on the first principal surface;
a holding portion including a joining surface directly joined to the second principal surface of the image pickup device substrate, and an inclined surface inclined inward at a predetermined angle relative to the joining surface; and
a wiring board including a distal end portion, an extending portion and a flexible portion disposed between the distal end portion and extending portion, the distal end portion being joined to the image pickup device substrate, the extending portion being jointed to the inclined surface of the holding portion via a bonding layer, and the flexure portion being flexed at the predetermined angle to permit the extending portion to be jointed to the inclined surface;
wherein the holding portion includes a block having a heat dissipation function;
the holding portion includes a recess portion or a through hole at the inclined surface;
the wiring board is a multilayer wiring board including at least a wiring layer on each of two surfaces thereof, an electronic component being mounted on each of the two surfaces; and
the electronic component mounted on the surface on the bonding layer side is disposed in the recess portion or via the through hole.

\* \* \* \* \*